United States Patent
Juujärvi et al.

(10) Patent No.: US 7,223,871 B2
(45) Date of Patent: May 29, 2007

(54) PROCESS FOR PREPARING SUBSTITUTED IMIDAZOLE DERIVATIVES AND INTERMEDIATES USED IN THE PROCESS

(75) Inventors: Päivi Juujärvi, Littoinen (FI); Seppo Parhi, Oulu (FI); Jaana Karjalainen, Oulu (FI)

(73) Assignee: Oy Juvantia Pharma Ltd., Turku (FI)

( * ) Notice: Subject to any disclaimer, the term of this patent is extended or adjusted under 35 U.S.C. 154(b) by 85 days.

(21) Appl. No.: 10/537,177

(22) PCT Filed: Jan. 8, 2004

(86) PCT No.: PCT/FI2004/000004

§ 371 (c)(1),
(2), (4) Date: Jun. 1, 2005

(87) PCT Pub. No.: WO2004/063168

PCT Pub. Date: Jul. 29, 2004

(65) Prior Publication Data
US 2006/0025465 A1    Feb. 2, 2006

(30) Foreign Application Priority Data
Jan. 8, 2003  (FI) .................................. 20030026

(51) Int. Cl.
*C07D 233/84* (2006.01)
*C07D 233/64* (2006.01)

(52) U.S. Cl. ............... 548/325.1; 548/341.5; 548/343.1; 548/346.1

(58) Field of Classification Search ........... 548/302.1, 548/325.1, 341.5, 343.1, 346.1
See application file for complete search history.

(56) References Cited
FOREIGN PATENT DOCUMENTS
EP       0 146 228      6/1985
EP       0 310 745      4/1989
WO       WO 01/17974    3/2001
WO       WO 03/099795   12/2003

OTHER PUBLICATIONS

Farmos-Yhtymä, *Chemical Abstracts* 113:231374 (1990).
Farmos-Yhtymä, *Chemical Abstracts* 116:143885 (1992).
*Schaumann, "Houben-Weyl Teil 3-E8C," Georg Thieme Verlag, Stuttgart, XP002282560, 40-41 (1994).

*Primary Examiner*—Joseph McKane
*Assistant Examiner*—Karen Cheng
(74) *Attorney, Agent, or Firm*—James C. Lydon

(57) ABSTRACT

The invention relates to a process for preparing substituted imidazole derivatives of formula (I) and acid addition salts thereof

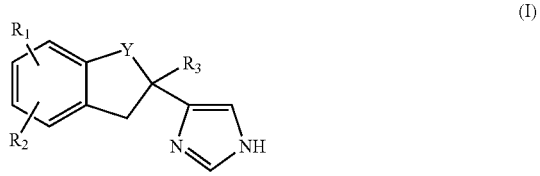

in which formula Y is —$CH_2$— or —CO—, $R_1$ is H, halo or hydroxy, $R_2$ is H or halo and $R_3$ is H or lower alkyl, starting from a compound of formula (II)

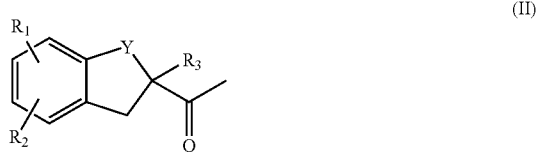

wherein Y, $R_1$, $R_2$ and $R_3$ are as defined above. The invention also relates to intermediates and their preparation.

12 Claims, No Drawings

PROCESS FOR PREPARING SUBSTITUTED IMIDAZOLE DERIVATIVES AND INTERMEDIATES USED IN THE PROCESS

FIELD OF THE INVENTION

The present invention relates to a new process for preparing substituted imidazole derivatives of formula (I) and acid addition salts thereof,

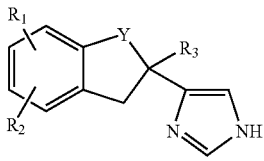

(I)

in which formula Y is —$CH_2$— or —CO—, $R_1$ is H, halogen or hydroxy, $R_2$ is H or halogen and $R_3$ is H or lower alkyl.

The invention also relates to intermediates used in the process and to their preparation.

BACKGROUND OF THE INVENTION

The compounds of the above-mentioned formula (I) are highly selective and long-acting antagonists of $\alpha_2$-adrenoceptors and they have a good peroral bioavailability. The compounds are especially valuable in the treatment of cognitive disorders. Compounds of formula (I) have been described in patent publication EP 0 618 906 B1. Specific examples of such compounds are 4-(2-ethyl-5-fluoroindan-2-yl)-1H-imidazole and 4-(5-fluoroindan-2-yl)-1H-imidazole.

The above-mentioned publication EP 0 618 906 B1 also discloses methods of preparing compounds of formula (I). Said methods relate to various ways of modifying the substituents in the benzene moiety of the indan ring system. There is no disclosure of a total synthesis, which would lead to the desired compounds in good yield.

Publication EP 0 310 745 B1 discloses a process for preparing compounds of formula (I), wherein the last step of the process comprises the use of formamide for the formation of the imidazole ring. The use of formamide, however, requires severe reaction conditions, which should be avoided in connection with industrial production in large scale.

Although the individual steps of the process according to the present invention are known as such (see e.g. EP 0 146 228 B1), it has now surprisingly been found that compounds of formula (I) can be prepared, also in large scale, in very good yields by using the synthesis route described below.

SUMMARY OF THE INVENTION

The present invention relates to a process for preparing substituted imidazole derivatives of formula (I) and acid addition salts thereof

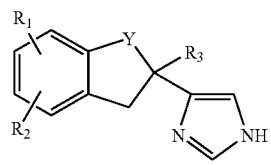

(I)

in which formula Y is —$CH_2$— or —CO—, $R_1$ is H, halogen or hydroxy, $R_2$ is H or halogen and $R_3$ is H or lower alkyl, comprising the steps of a) halogenating a compound of formula (II)

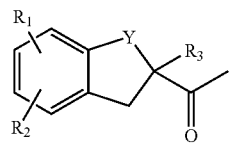

(II)

wherein Y, $R_1$, $R_2$ and $R_3$ are as defined above, to obtain a compound of formula (III)

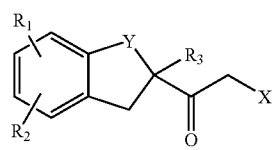

(III)

wherein Y, $R_1$, $R_2$ and $R_3$ are as defined above and X is halogen, b) reacting the compound of formula (III) thus obtained with an amine of formula $R_4NH_2$, wherein $R_4$ is an easily removable leaving group, and an alkali metal thiocyanate, to obtain a compound of formula (IV)

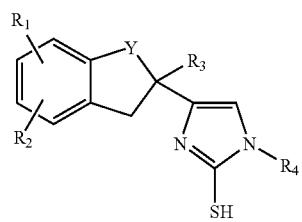

(IV)

wherein Y, $R_1$, $R_2$, $R_3$ and $R_4$ are as defined above, c) removing the mercapto group from the compound of formula (IV) to obtain a compound of formula (V)

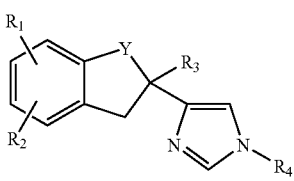

wherein Y, $R_1$, $R_2$, $R_3$ and $R_4$ are as defined above, d) removing the group $R_4$ from the compound of formula (V) to obtain a compound of formula (I), and, if desired, e) converting the resulting compound of formula (I) into an acid addition salt thereof.

Further the invention relates to a process for preparing a compound of formula (IV)

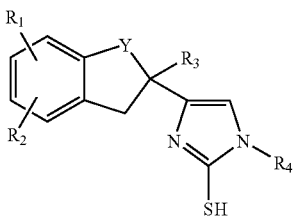

wherein Y is —$CH_2$— or —CO—, $R_1$ is H, halogen or hydroxy, $R_2$ is H or halogen and $R_3$ is H or lower alkyl, comprising reacting a compound of formula (III)

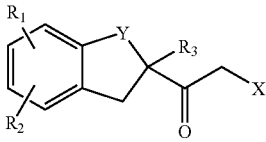

wherein Y, $R_1$, $R_2$ and $R_3$ are as defined above and X is halogen, with an amine of formula $R_4NH_2$, wherein $R_4$ is an easily removable leaving group, and an alkali metal thiocyanate.

The invention also relates to intermediate compound (IV) wherein Y, $R_1$, $R_2$, $R_3$ and $R_4$ are as defined above.

DETAILED DESCRIPTION OF THE INVENTION

In this context, the term an acid addition salt refers to an addition salt of any pharmaceutically acceptable acid, preferably hydrochloric or hydrobromic acid.

In this context, the term halogen refers to F, Cl, Br and I. Regarding $R_1$ and/or $R_2$ it preferably refers to F and/or Cl, and most preferably to F. Regarding X it preferably refers to Cl and Br, and most preferably to Br.

In this context, the term lower alkyl refers to a monoradical branched or unbranched saturated hydrocarbon chain having from 1 to 6 carbon atoms, preferably 1 to 4 carbon atoms and most preferably 1 or 2 carbon atoms.

In this context the term aralkyl refers to substituted or unsubstituted groups -alkylene-aryl. Alkylene refers to a diradical of a branched or unbranched saturated hydrocarbon chain, preferably having from 1 to 10 carbon atoms and more preferably having 1 to 6 carbon atoms and aryl refers to an unsaturated aromatic carbocyclic group of from 6 to 20 carbon atoms having a single ring (e.g. phenyl) or multiple condensed (fused) rings (e.g. naphthyl or anthryl).

In this context the term easily removable leaving group refers to any group that a person skilled in the art would know to be easily removable. Preferred easily removable leaving groups would be aralkyls, e.g. benzyl.

According to the present invention a compound of formula (II) is, in step a), halogenated with a halogenating agent to obtain a compound of formula (III), where X is a halogen, e.g. Br, Cl or I. A preferred halogenating agent is $Br_2$. The reaction is suitably carried out in a solvent, such as an alcohol, e.g. methanol, at room temperature or below. A suitable temperature is −8° C. to +25° C., preferably −8° C. to −5° C.

In step b) the compound of formula (III) obtained in step a) is reacted with an amine of formula $R_4NH_2$ where $R_4$ is a easily removable leaving group, and an alkali metal thiocyanate to obtain a mercapto compound of formula (IV). The reaction is suitably carried out in a solvent, such as as an alcohol, e.g. ethanol or butanol, at an elevated temperature, preferably at reflux temperature. The amine for the reaction may be one where $R_4$ is aralkyl, preferably benzyl. A preferred alkali metal thiocyanat is potassium thiocyanate.

In step c) the mercapto group is removed from the compound of formula (IV) obtained in step c) to obtain a compound of formula (V). The reaction is suitably carried out in the presence of a catalyst, e.g Raney-Nickel, at a temperature of 40° C. to 90° C., preferably 40° C. to 60° C.

In step d) the group $R_4$ can be removed from the compound of formula (V) obtained in step c) by treating the compound of formula (V) with ammonium formate in the presence of a catalyst, such as Pd/C. Alternatively a catalyst, such as Raney-Nickel, may be used, or $R_4$ may be removed by hydrogenation in the presence of Pd/C.

The resulting compound of formula (I) may be converted into acid addition salts using methods known per se. Preferred acid addition salts are HCl and HBr.

Preferred compounds of formulae (I) to (V) are those where Y is $CH_2$, $R_1$ is F, $R_2$ is H and $R_3$ is ethyl.

The process according to the present invention makes it possible to prepare compounds of formula (I) in good yield and in a simple way, e.g. by using lower reaction temperatures, that also are suitable for large-scale production. The known methods result in poor yields and require severe reaction conditions, e.g. high temperatures, which makes large-scale production difficult. For instance, compared to the process using formamide (EP 0 310 745 B1), the process of the present invention using lower temperatures does not create separation or isolation problems relating to great amounts of various impurities that are typically formed in the known formamide process The following examples illustrate the invention, but are not intended to restrict the scope of the invention.

EXAMPLE 1

2-bromo-1-(2-ethyl-5-fluoro-indan-2-yl)-ethanone 3.8 g of 2-acetyl-2-ethyl-5-fluoroindan and 35 ml of methanol were placed into a round-bottomed flask equipped with a thermometer, a mechanical stirrer and a dropping funnel. The reaction mixture was cooled in a cooling bath while stirring to a temperature between −5° C. and −8° C. and 0.7 ml of a $Br_2$-solution in a small amount of methanol was added dropwise. The cooling bath was removed and the reaction mixture was stirred at room temperature for 2 hours. The reaction mixture was cooled to a temperature between −5° C. and −8° C. and an additional 0.175 ml of $Br_2$-solution in a small amount of methanol was added dropwise. The cooling bath was removed and the reaction mixture was stirred at room temperature for an additional 1 to 2 hours. After chromatographic purification using methylene chloride as an eluent 2.51 g of 2-bromo-1-(2-ethyl-5-fluoro-indan-2-yl)-ethanone was obtained as a liquid (yield 69%).

1H NMR (200 MHz, CDCl3, ppm): 0.85 (3H, t, J 7.6 Hz, CH2CH3), 1.82 (2H, q, J 7.5 Hz, CH2CH3), 2.83–2.93 (2 H, dd, the indan ring H2-1 or H2-3), 3.32–3.46 (2 H, dd, the indan ring H2-1 or H2-3), 4.11 (2H, s, CH2-Br), 6.79–7.10 (3H, m, Ar—H)

HPLC-MS: 285–286–287 (68, M+, Br-isotopes), 205 (72), 187 (100). UV (Lambda-max): 208 nm (Abs. 1.01020 AU), 271 nm (Abs. 0.27428 AU), 277 nm (Abs. 0.27026 AU).

EXAMPLE 2

1-benzyl-5-(2-ethyl-5-fluoro-indan-2-yl)-imidazole-2-thiol 1.62 g of 2-bromo-1-(2-ethyl-5-fluoro-indan-2-yl)-ethanone was dissolved in 25 ml of ethanol in a glass round-bottomed flask equipped with a mechanical stirrer, a thermometer and a dropping funnel. The reaction mixture was heated to reflux temperature while stirring. 0.366 g of benzylamine dissolved in 5 ml ethanol was added slowly in a drop-wise fashion to the solution. After the addition of benzylamine the mixture was refluxed for one hour. 0.330 g of potassium thiocyanate was added portionwise during 30 minutes and the reaction mixture was refluxed for 2 hours. The reaction mixture was evaporated to dryness before 150 ml ethyl acetate was added and the solution was washed with water. The organic phase was dried over $Na_2SO_4$, filtered and evaporated providing 1.13 g of 1-benzyl-5-(2-ethyl-5-fluro-indan-2-yl)-imidazole-2-thiol (yield 31%). The analytical sample was purified using TLC-plates. The purity was measured by HPLC: 62%. Normally the crude product was used in the following step.

1H NMR (200 MHz, $CDCl_3$, ppm): 0.75 (t, $CH_2CH_3$), 1.80 (q, $CH_2CH_3$), 2.81–3.30 (m, the indan ring $H_2$-1 and $H_2$-3), 5.18 (s, N—$CH_2$—Ar), 6.24 (s, —SH), 6.77–7.09 (m, Ar—H, im-H), 7.23–7.36 (m, Ar—H—$CH_2$—N).

HPLC-MS: 353 (100, M+), 221 (29), 187 (12).

EXAMPLE 3

1-benzyl-5-(2-ethyl-5-fluoro-indan-2-yl)-imidazole 7.5 ml of Raney-Nickel prepared according to Vogel, Practical Organic Chemistry, 5$^{th}$ Edition, 1999, Longman, U.K. p. 450–451, was mixed with 20 ml of ethanol under nitrogen atmosphere in a round-bottomed flask equipped with a thermometer and a stirring bar. 500 mg of 1-benzyl-5-(2-ethyl-5-fluoro-indan-2-yl)-imidazole-2-thiol was dissolved in 10 ml of ethanol and added to the mixture. The reaction mixture was stirred at 40° C. for about 10 hours and then the temperature was raised to 60° C. for 2 hours followed by cooling to room temperature. The mixture was filtered and the filter (Celite™) was washed with ethanol. The ethanol solution was evaporated to dryness to obtain 151 mg of a crude product. After chromatographic purification using methylene chloride, methylene chloride:methanol (10:1) and methylene chloride:methanol (1:1) as eluents 1-benzyl-5-(2-ethyl-5-fluoro-indan-2-yl)-imidazole was obtained. The purity was measured by HPLC: 83%.

1H NMR (200 MHz, MeOD, ppm): 0.70 (3H, t, $CH_2CH_3$), 1.82 (2H, q, $CH_2CH_3$), 2.90–3.01 (2 H, dd, the indan ring $H_2$-1 or $H_2$-3), 3.13–3.25 (2 H, dd, the indan ring $H_2$-1 or $H_2$-3), 5.10 (2H, s, N—$CH_2$—Ar), 6.72–6.87 (3H, m, Ar—H, im-H), 7.05–7.18 (3H, m, Ar—H, Ar—H—$CH_2$—N), 7.29–7.32 (3H, m, Ar—H—$CH_2$—N), 7.56 (1H, s, im-H).

HPLC-MS: 321 (100, M+).

EXAMPLE 4

4-(2-ethyl-5-fluoro-indan-2-yl)-1H-imidazole 53 mg of 1-benzyl-5-(2-ethyl-5-fluoro-indan-2-yl)-imidazole, 20 mg of Pd/C, 51 mg of ammonium formate and 2 ml of ethanol were added under nitrogen atmosphere into a round-bottomed flask equipped with a thermometer and a stirring bar. The reaction mixture was stirred at reflux temperature for 6 hours. The mixture was filtered and the filter (Celite™) was washed with ethanol. The reaction mixture was placed back into a round-bottomed flask and an additional 20 mg of Pd/C and 51 mg of ammonium formate were added under nitrogen atmosphere. The mixture was heated to reflux temperature and refluxed for 2 hours. Then the mixture was cooled to room temperature and filtered. The filter (Celite™) was washed with ethanol and after evaporation to dryness, whereby 4-(2-ethyl-5-fluoro-indan-2-yl)-1H-imidazole was obtained. The analytical sample was purified using TLC-plates. The purity was measured by HPLC: 60%. Normally the crude product was used in the following step.

1H NMR (200 MHz, MeOD, ppm): 0.76 (t, $CH_2CH_3$), 1.29 (q, $CH_2CH_3$), 2.98–3.22 (m, the indan ring $H_2$-1 and $H_2$-3), 6.78–6.94 (m, Ar—H, im-H), 7.09–7.19 (m, Ar—H, im-H).

HPLC-MS: 231 (100, M+).

EXAMPLE 5

4-(2-ethyl-5-fluoro-indan-2-yl)-1H-imidazole 10 ml of the crude product obtained in Example 3 was placed in a round-bottomed flask equipped with a thermometer and a stirring bar. 1.5 ml of Raney-Nickel in ethanol (Raney-Nickel prepared according to Vogel, Practical Organic Chemistry, 5$^{th}$ Edition, 1999, Longman, U.K. p. 450–451), was added under nitrogen atmosphere. The reaction mixture was stirred at reflux temperature for about 14 hours. After filtration and evaporation crude 4-(2-ethyl-5-fluoro-indan-2-yl)-1H-imidazole was obtained.

HPLC-MS: 231 (100, M+).

EXAMPLE 6

4-(2-ethyl-5-fluoro-indan-2-yl)-1H-imidazole-hydrochloride

A HCl/methanol reagent was prepared by bubbling HCl-gas through methanol. 100 mg of 4-(2-ethyl-5-fluoro-indan-2-yl)-1H-imidazole was dissolved in 2 ml methanol in a round-bottomed flask. 2 ml of HCl/methanol reagent (3 M)

was added slowly to the solution while stirring. During the addition the internal temperature of the mixture was kept below 29° C. by cooling. The resulting mixture was evaporated at a temperature between 35° C. and 40° C. to viscous colourless oil whereupon it was dissolved in 2 ml of acetone at the same temperature. The solution was cooled to a temperature between 10° C. and 15° C. at which temperature the mixture started to crystallize. The crystalline material was filtered, washed with cooled acetone and dried in a vacuum oven at 35° C. overnight. A second crop was isolated from the mother liquid followed by cooling, filtering and drying as described above. The yield of 4-(2-ethyl-5-fluoro-indan-2-yl)-1H-imidazole-hydrochloride was altogether 87% of the theoretical, m.p. 171–173° C.

What is claimed is:

1. A process for preparing compounds of formula (I) and acid addition salts thereof

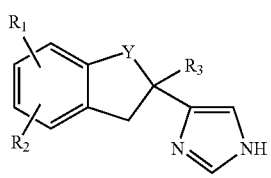
(I)

in which Y is —CH$_2$— or —CO—, R$_1$ is H, halogen or hydroxy, R$_2$ is H or halogen and R$_3$ is H or lower alkyl, comprising the steps of a) halogenating a compound of formula (II)

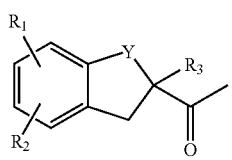
(II)

wherein Y, R$_1$, R$_2$ and R$_3$ are as defined above, to obtain a compound of formula (III)

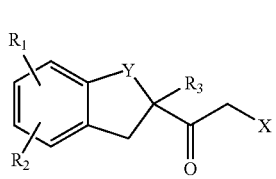
(III)

wherein Y, R$_1$, R$_2$ and R$_3$ are as defined above and X is halogen, b) reacting the compound of formula (III) thus obtained with an amine of formula R$_4$NH$_2$, wherein R$_4$ is an aralkyl group, and an alkali metal thiocyanate to obtain a compound of formula (IV)

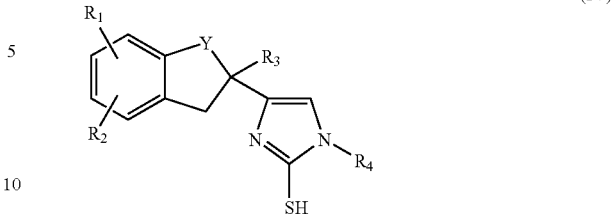
(IV)

wherein Y, R$_1$, R$_2$, R$_3$ and R$_4$ are as defined above, c) removing the mercapto group from the compound of formula (IV) to obtain a compound of formula (V)

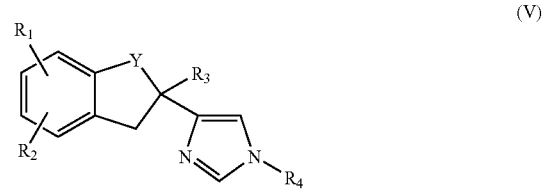
(V)

wherein Y, R$_1$, R$_2$, R$_3$ and R$_4$ are as defined above, d) removing the group R$_4$ from the compound of formula (V) to obtain a compound of formula (I), and, if desired, e) converting the resulting compound of formula (I) into an acid addition salt thereof.

2. A process according to claim 1 wherein step a) is carried by reacting a compound of formula (II) with Br$_2$ in methanol at a temperature of −8 to +25° C.

3. A process according to claim 1 wherein step b) is carried out by reacting a compound of formula (III) with benzylamine and potassium thiocyanate.

4. A process according to claim 1 wherein step c) is carried out in the presence of Raney-Nickel at a temperature of 40° C. to 90° C.

5. A process according to claim 1 wherein step d) is carried out by using ammonium formate in the presence of Pd/C.

6. A process according to claim 1 wherein step d) is carried out by hydrogenation in the presence of Pd/C.

7. A process according to claim 1 wherein Y is —CH$_2$—, R$_1$ is F, R$_2$ is H and R$_3$ is ethyl.

8. A process for preparing a compound of formula (IV)

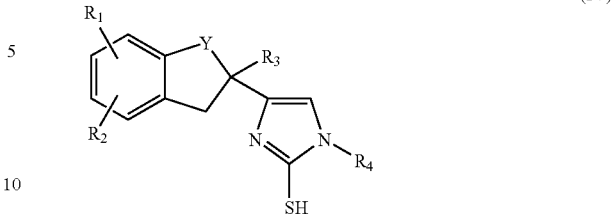
(IV)

wherein Y is —CH$_2$— or —CO—, R$_1$ is H, halogen or hydroxy, R$_2$ is H or halogen and R$_3$ is H or lower alkyl, comprising reacting a compound of formula (III)

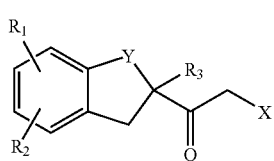

wherein Y, $R_1$, $R_2$ and $R_3$ are as defined above and X is halogen, with an amine of formula $R_4NH_2$, wherein $R_4$ is an aralkyl group, and an alkali metal thiocyanate.

9. A process according to claim 8 comprising reacting a compound of formula (III) with benzylamine and potassium thiocyanate.

10. A process according to claim 8 wherein Y is —$CH_2$—, $R_1$ is F, $R_2$ is H and $R_3$ is ethyl.

11. A compound of formula (IV)

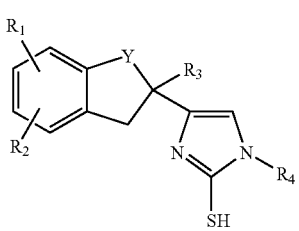

wherein Y is —$CH_2$— or —CO—, $R_1$ is halogen or hydroxy, $R_2$ is H or halogen, $R_3$ is H or lower alkyl and $R_4$ is an aralkyl group.

12. A compound according to claim 11 wherein Y is —$CH_2$—, $R_1$ is F, $R_2$ is H, $R_3$ is ethyl and $R_4$ is benzyl.

* * * * *

UNITED STATES PATENT AND TRADEMARK OFFICE
CERTIFICATE OF CORRECTION

PATENT NO. : 7,223,871 B2 Page 1 of 1
APPLICATION NO. : 10/537177
DATED : May 29, 2007
INVENTOR(S) : Paivi Juujarvi, Seppo Parhi and Jaana Karjalainen It is certified that error appears in the above-identified patent and that said Letters Patent is hereby corrected as shown below:

IN THE CLAIMS:

Claim 4, Col. 8, line 43, change "40° C." to -- 40° C --.

Claim 12, Col. 10, line 17, change "—$CH_2$—$R_1$ is" to -- —$CH_2$—, $R_1$ is --.

Signed and Sealed this

Twenty-fifth Day of March, 2008

JON W. DUDAS
*Director of the United States Patent and Trademark Office*